(12) United States Patent
Hartwig (10) Patent No.: US 9,408,802 B1
(45) Date of Patent: Aug. 9, 2016

(54) SEVEN DAY DRUG IN ADHESIVE TRANSDERMAL DELIVERY

(71) Applicant: ProSolus, Inc., San Antonio, TX (US)

(72) Inventor: Rod L. Hartwig, Cooper City, FL (US)

(73) Assignee: ProSolus, Inc., San Antonio, TX (US)

( * ) Notice: Subject to any disclaimer, the term of this patent is extended or adjusted under 35 U.S.C. 154(b) by 307 days.

(21) Appl. No.: 13/848,865

(22) Filed: Mar. 22, 2013

Related U.S. Application Data

(60) Provisional application No. 61/614,133, filed on Mar. 22, 2012.

(51) Int. Cl.
*A61K 9/70* (2006.01)
*A61F 13/02* (2006.01)
*A61K 9/00* (2006.01)

(52) U.S. Cl.
CPC .................................. *A61K 9/0014* (2013.01)

(58) Field of Classification Search
None
See application file for complete search history.

(56) References Cited

U.S. PATENT DOCUMENTS

| 5,676,968 | A | * | 10/1997 | Lipp et al. | 424/448 |
| 2006/0078604 | A1 | * | 4/2006 | Kanios et al. | 424/449 |
| 2010/0178323 | A1 | * | 7/2010 | Kydonieus et al. | 424/448 |
| 2011/0054043 | A1 | * | 3/2011 | Funaki et al. | 514/772.4 |

* cited by examiner

*Primary Examiner* — Robert A Wax
*Assistant Examiner* — Randeep Singh
(74) *Attorney, Agent, or Firm* — Dority & Manning, P.A.

(57) ABSTRACT

A transdermal formulation and method of treatment includes providing an active pharmaceutical ingredient, a poly-isobutylene or silicone PSA, optionally, an oil, a crosslinked polyvinylpyrrolidone, and optionally, silicon dioxide, wherein said formulation is prepared on a backing in a three layer transdermal delivery system formulated to provide transdermal delivery and therapeutic levels for up to seven days and optionally with an overlay system required to show bioequivalence.

7 Claims, 7 Drawing Sheets

SEVEN DAY DRUG IN ADHESIVE TRANSDERMAL DELIVERY

INDEX TO RELATED APPLICATIONS

This application claims benefit to and is a non-provisional application of U.S. Provisional Patent Application No. 61/614,133 filed Mar. 22, 2012 the disclosure of which is incorporated herein by reference in its entirety.

BACKGROUND OF THE INVENTION

Bioavailability and bioequivalence are parameters that are often elusive to a pharmaceutical formulations scientist. The scientist is faced with many industry and regulatory constraints in which formulations are developed. In particular, there are composition patent constraints to which one skilled in the art must formulate around in order to achieve a pharmaceutically accepted bioequivalent product.

The present invention is directed to compositions for topical or transdermal delivery of active pharmaceutical agents and methods of using compositions. In particular, the present invention has achieved significant advancement in utilization of a preferred combination of crosslinked polyvinylpyrrolidone with or without the addition of silicon dioxide to achieve a desired drug release of an active pharmaceutical ingredient (API) in a transdermal drug-in-adhesive patch formulation.

SUMMARY OF THE INVENTION

The use of a drug delivery composition, such as a topical, transdermal, or transmucosal composition containing a medicament (e.g. an active pharmaceutical ingredient, API or drug), as a means for administering topically, locally or systemically therapeutically effective amounts of the medicament is well known. Topical compositions may include liquids, creams, lotions, salves, pastes, balms, gels and ointments. Transdermal or transmucosal compositions include flexible-finite systems, such as patches. A typical patch embodiment may comprise a transdermal carrier, such as a polymeric pressure-sensitive adhesive composition or bio-adhesive composition, and the medicament. In some cases, the medicament is comprised in the transdermal carrier, such as by the formation of a dispersion, solution or blend of the transdermal carrier formulation and the drug. The function of the adhesive composition of the patch embodiment is to adhere the patch to the skin or mucosa, and as a carrier substrate for the medicament. Generally, the adhesive adheres effectively to the skin or mucosa and permits permeation, diffusion and/or migration of the medicament from the carrier to the site of application and/or through the skin or mucosa into the local area of application, and/or through the skin or mucosa into the bloodstream of the patient for systemic circulation of the medicament.

Topical or transdermal (or transmucosal) drug delivery permits controlled release of a drug into a patient without directly invading the patient's body. This mode of administration can conveniently and effectively deliver drug doses in a passive and continuous manner over the course of hours, days, or weeks. Typically, a transdermal drug delivery composition can be placed anywhere on the skin, including sites typically concealed by clothing, and is therefore discreet and cosmetically elegant. Its ease of use also increases patient compliance with drug administration. For example, an individual does not have to adhere to a strict oral regimen, perform routine injections or travel to a clinic for treatment.

Topical, local, and transdermal delivery compositions can be designed to achieve particular blood level profiles of the drug, such as steady-state blood level profiles or increasing blood level profiles, such as may be desired for a particular drug or condition. Moreover, the release rate of the drug can be controlled, for example, by the selection of the polymers used in the carrier composition and other components, such as permeation enhancers, solubility enhancers, co-solvents, dispersion agents, crystallization inhibitors, and other components that are well known in the art.

For these and other reasons, a topically, locally, or transdermally formulated drug is often perceived as more desirable than traditional drug delivery systems, such as injectable formulations and orally-administered tablets. However, it can be difficult to formulate a drug into a composition that will effectively pass through the outer layers of the skin for therapeutically effective administration. For example, certain drugs require additional modification of the transdermal adhesive or bio-adhesive composition in order to enhance the delivery of the medicament through the skin or mucosa. This may require the use of certain and defined components, through appropriate experimental design, which may include but not limited to: permeation enhancers, solubility enhancers, co-solvents, dispersion agents, crystallization inhibitors, and other components that are well known in the art that modify the delivery rate of medicaments. In another aspect of formulation, it is important to control the delivery throughout the delivery period, and thus the need to modify the formulation to reduce, i.e. control, the delivery throughout the delivery profile is required. Typically, maximum permeation through the skin is preferred to ensure the smallest patch size. In this case, it is necessary to reduce the long term drug delivery to ensure bioequivalence to the reference listed drug is obtained. The definition of these components and the preferred medicaments for which they pertain to; and of which are physically and chemically stable; and of which are deliverable from the substrate composition are of interest to the inventor.

In the present invention, one novelty is the use of crospovidone as a rate controlling excipient to curb the onset of the initial dump and to provide the sustained delivery of the agent to provide a bioequivalent formulation to a control RLD.

Typically, when adding rate controlling agents if you decrease the dump you can maintain the sustainability, but you usually lose the "total" drug delivered (I.E. AUC), i.e. make patch size bigger or have to load more drug. The composition of the present invention provides same amount of drug as the innovator, and decrease the dump to match the Cmax, and keep the sustainability (duration) with the same patch size as the innovator. This is a novel and unexpected result. The "binder" in a preferred embodiment is crosslinked PVP.

In one embodiment, the present invention is a transdermal formulation comprising:
 an active pharmaceutical ingredient;
 at least one of an elastomer or pressure sensitive adhesive;
 optionally, one of an oil or fluid;
 a binder;
 optionally a filler;
wherein said formulation is prepared on a backing in a multi layer transdermal delivery system imparting transdermal delivery of said active pharmaceutical ingredient at therapeutic levels for a time period of up to seven days, said release dependent on concentration of said binder and optionally a filler.

In one embodiment, the active pharmaceutical ingredient is Clonidine or Rotigotine.

The formulation includes optionally, a mineral oil or Silicone fluid.

In one embodiment, the formulation incorporates a binder that is a cross-linked polymer.

The formulation, in one embodiment provides the crosslinked polymer as crosslinked polyvinylpyrrolidone (crospovidone).

The formulation filler, in one embodiment, is silicon dioxide.

In one embodiment, the elastomer or pressure sensitive adhesive is Polyisobutylene or Silicone pressure sensitive adhesive (PSA) which is any of an amine compatible, an amine incompatible, standard grade silicone PSA, or combinations thereof.

In one embodiment, the formulation of the present invention comprises:
  about 0.1-15% wilw of an active pharmaceutical ingredient;
  about 50-99.6% w/w of an elastomer or pressure sensitive adhesive;
  optionally, about 0-20% w/w of an oil;
  about 0.1-15% w/w of a binder; and
optionally about 0.1-15% w/w of a filler.
  Preferably, the formulation is consisting essentially of:
about 6% clonidine;
about 5% crospovidone;
about 1% silicon dioxide;
about 10% mineral oil; and
about 78% polyisobutylene.

In one embodiment, the formulation comprises:
  about 0.1-15% w/w of an active pharmaceutical ingredient;
  about 50-99.6% w/w of a silicone pressure sensitive adhesive;
  optionally, about 0-20% w/w of a silicone fluid;
  about 0.1-15% w/w of a binder; and
optionally; about 0-15% w/w of a filler.
  Preferably, the formulation consists essentially of:
about 4 to 10% Rotigotine;
about 5% Crospovidone;
about 89% Silicone PSA standard grade non-amine compatible.

In one embodiment, the concentration of silicon dioxide in relation to an amount of crosslinked polyvinylpyrrolidone is varied and controls the delivery rate of the active pharmaceutical ingredient at ratio of silicon dioxide to cross-linked polyvinylpyrrolidone is from about 0.1:1 to about 1:1.

In another embodiment, the concentration of silicon dioxide in relation to an amount of crosslinked polyvinylpyrrolidone is varied and controls the delivery rate of the active pharmaceutical ingredient at ratio of silicon dioxide to cross-linked polyvinylpyrrolidone is from about 1:1 to about 1:10.

In another embodiment, the concentration of silicon dioxide in relation to an amount of crosslinked polyvinylpyrrolidone is varied and controls the delivery rate of the active pharmaceutical ingredient at ratio of silicon dioxide to cross-linked polyvinylpyrrolidone is from about 1:1 to about 1:5 in a preferred embodiment of a clonidine formulation.

In another embodiment, the concentration of silicon dioxide in relation to an amount of crosslinked polyvinylpyrrolidone is varied and controls the delivery rate of the active pharmaceutical ingredient at ratio of silicon dioxide to cross-linked polyvinylpyrrolidone is from about 0.1:5 to about 1:20 in a preferred embodiment of a Rotigotine formulation.

In another embodiment, the concentration of silicon dioxide in relation to an amount of crosslinked polyvinylpyrrolidone is varied and controls the delivery rate of the active pharmaceutical ingredient at ratio of silicon dioxide to cross-linked polyvinylpyrrolidone is from about 0.1:1 to about 1:5 in a preferred embodiment of a Rotigotine formulation.

The present invention includes a method of providing transdermal delivery and therapeutically effective levels for up to seven days comprising:
  providing a transdermal delivery patch formulated according to the present invention;
  affixing said patch to a patient;
  transdermally delivering an active pharmaceutical ingredient to a patient resulting from said affixing, wherein said affixed patch remains affixed for up to a seven day dosing period.

BRIEF DESCRIPTION OF THE SEVERAL VIEWS OF THE DRAWINGS

FIG. 2.1 is a release profile of Flux v. time of embodiments of the present invention.
FIG. 3.1 is a release profile of Flux v. time of embodiments of the present invention.
FIG. 4.1 is a release profile of Flux v. time of embodiments of the present invention.

DETAILED DESCRIPTION OF THE PREFERRED EMBODIMENT

The invention pertains to the development of a formulation that comprises a 3-layer system for a 7-day delivery of a drug-in-adhesive system for transdermal delivery of clonidine. An overlay is used on top of the system as required for bio-equivalency.

One known formulation based on review of prior art comprises the following in the logical order from Top (Overlay), backing layer, Adhesive layer (reservoir), rate controlling membrane, Adhesive layer (for adhering to the skin), and the disposable Release Liner.
  Layer 1: OVERLAY SYSTEM
  Layer 2: BACKING LAYER
  Layer 3: comprises a blended formulation of the following:
CLONIDINE BASE
POLYISOBUTYLENE
MINERAL OIL
SILICON DIOXIDE
  Layer 4: A RATE CONTROLLING MEMBRANE
  Layer 5: comprises a blended formulation of the following:
CLONIDINE BASE
POLYISOBUTYLENE
MINERAL OIL
SILICON DIOXIDE
  Layer 6: Disposable Release Liner
  In one embodiment, a preferred formulation based on experimental design comprises and/or contains the following:
  Layer 1: Overlay System
  Layer 2: Backing Layer
  Layer 3: comprises a blended formulation of the following:
CLONIDINE BASE
POLYISOBUTYLENE
MINERAL OIL
SILICON DIOXIDE
CROSSLINKED POLYVINYLPYRROLIDONE (CROSPOVIDONE)

Layer 4: Disposable Release Liner

The delivery system of the present invention has been demonstrated using Clonidine. It is contemplated in the present formulation using crosslinked polyvinylpyrrolidone to general applicability to other Active Pharmaceutical Ingredients (APIs) which exhibit similar solubility and chemical moeities (i.e. 2nd and/or $3^{rd}$ amine(s), and/or combinations thereof) as compared to this API. One point of novelty of the formulation of the present invention is that the formulation contains a crosslinked polyvinylpyrrolidone, which has been discovered to be a surprisingly good excipient for the control of the delivery of Clonidine. Additionally, it has been discovered that a combination of crosslinked polyvinylpyrrolidone with a specific concentration of a certain grade of silica dioxide controls the delivery of Clonidine as well in a preferred formulation. This enhancement of delivery was proven through in vitro human cadaver skin permeation studies over other materials known to those skilled in the art.

Although the present invention was tested as set forth herein, in vitro human cadaver skin permeation studies are known to those skilled in the art and variations of the testing parameters are contemplated to yield similar positive results.

Progress of the development of the preferred formulation consisted of step-wise formulation of the known formulation containing a poly-isobutylene pressure sensitive adhesive with similar excipients found in the innovator product, i.e API, Mineral Oil, polyisobutylene, and silicon dioxide. Formulations were prepared decidedly to eliminate the rate controlling membrane, and to make a single adhesive layer system as compared to the multi-layer systems which are commercially available. This single adhesive layer also provides for limiting the manufacturing process to a single pass vs. multiple passes for manufacturing the currently available products. Surprisingly, it was found that the addition of crosslinked polyvinylpyrrolidone was required to ensure delivery level was achieved and was sustained throughout the delivery period from a single layered adhesive transdermal drug delivery system.

For reference:

PIB PSA 87-608A=Polyisobutylene formulated pressure sensitive adhesive

Acrylic PSA 87-9301=Non-functional Amine acrylic pressure sensitive adhesive

Acrylic PSA 87-502A=Acrylic–Rubber Copolymer pressure sensitive adhesive

Acrylic PSA 87-2852=Carboxy (—COOH)functional Acrylic pressure sensitive adhesive Silicone PSA 7-4502=Silicone Pressure sensitive adhesive Skin Permeation Study #0001:

Initial formulations (002-7-1 to 5) were formulated to contain less API than the innovator. Formulations were made to simply identify formulations activities could be evaluated on dispersed, micronized, API within a matrix with almost the same excipients.

| Ingredients | 7-1 | 7-2 | 7-3 | 7-4 | 7-5 |
|---|---|---|---|---|---|
| Clonidine Base | 5% | 5% | 5% | 5% | 5% |
| PIB PSA 87-608A | 95% | 90% | 85% | 80% | 80% |
| Mineral Oil | | 5% | 10% | 10% | 10% |
| Silica Dioxide | | | | 5% | |
| Crospovidone | | | | | 5% |

Formulations (002-8-1 to 4) were formulated to determine the effect of the type of PVP on the system. Formulas 1 and 2, containing no PVP and Crosslinked PVP, respectively, both had uniform crystal dispersion throughout the laminate samples. Both 3 and 4, containing standard soluble PVP, and co-polymer soluble VA-PVP, respectively, both exhibited non-uniform crystal growth throughout the matrix.

| Ingredients | 8-1 | 8-2 | 8-3 | 8-4 |
|---|---|---|---|---|
| Clonidine Base | 5% | 5% | 5% | 5% |
| PIB PSA 87-608A | 90% | 80% | 80% | 80% |
| Mineral Oil | 5% | 10% | 10% | 10% |
| Crospovidone | | 5% | | |
| Povidone 29/32 | | | 5% | |
| Povidone VA/PVP | | | | 5% |

Figure 1:
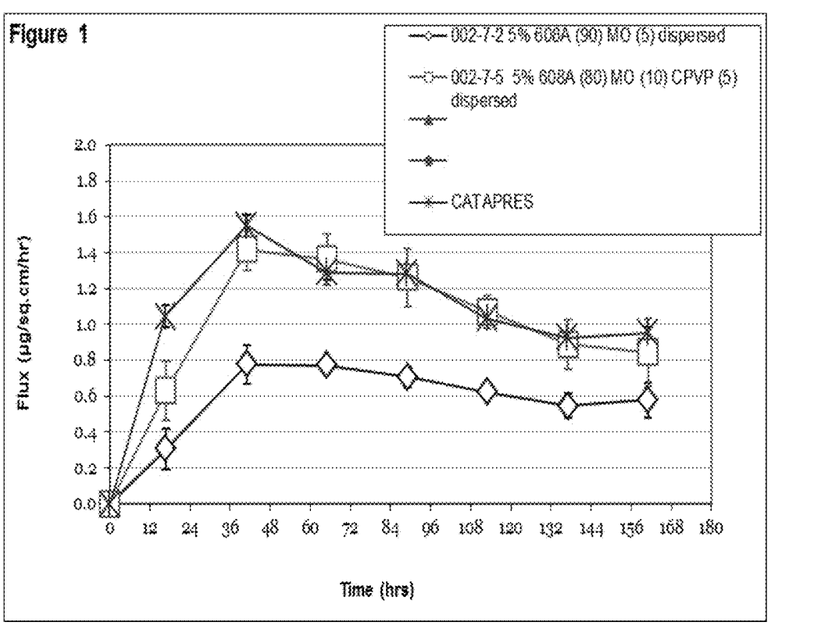
FIG. 1 is a release profile of Flux v. time of embodiments of the present invention.
Figure 2:
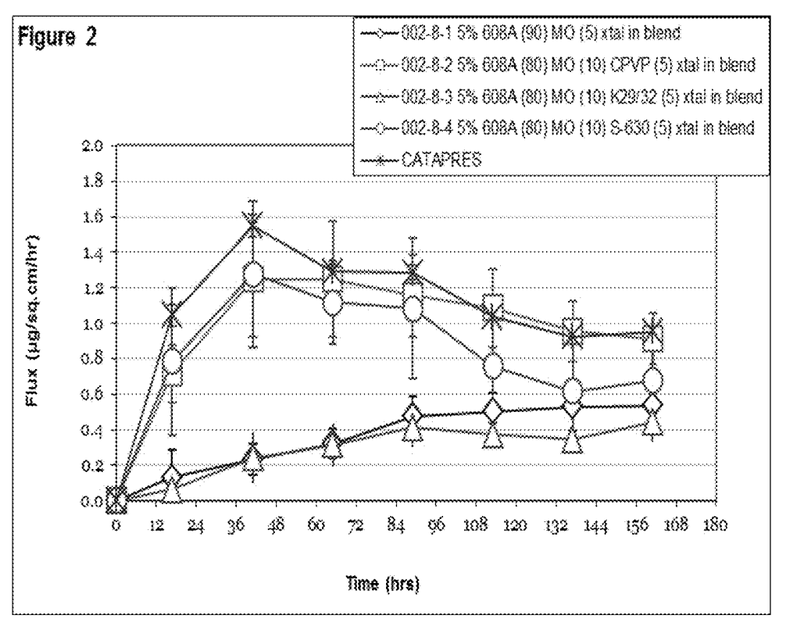
FIG. 2 is a release profile of Flux v. time of embodiments of the present invention.

Attached Figures show the results of the 1st skin permeation study for the above formulations compared to CATAPRES® TTS-3. As can be seen in FIG. 1, 002-7-5 was the closest to the innovator product in AUC and C-Max. FIG. 2 shows that the insoluble PVP is the only formulation which maintains the delivery through 7 days comparable to the control formulation. The copolymer soluble grade of VA-PVP in formulation 002-8-4 exhibits the same C-Max, but total AUC is diminished after the 7 days of delivery. Both the formulations containing no PVP (002-8-1) derivative and standard soluble PVP (002-8-3) exhibit significantly reduced flux throughout the 7 days.

Figure 3:
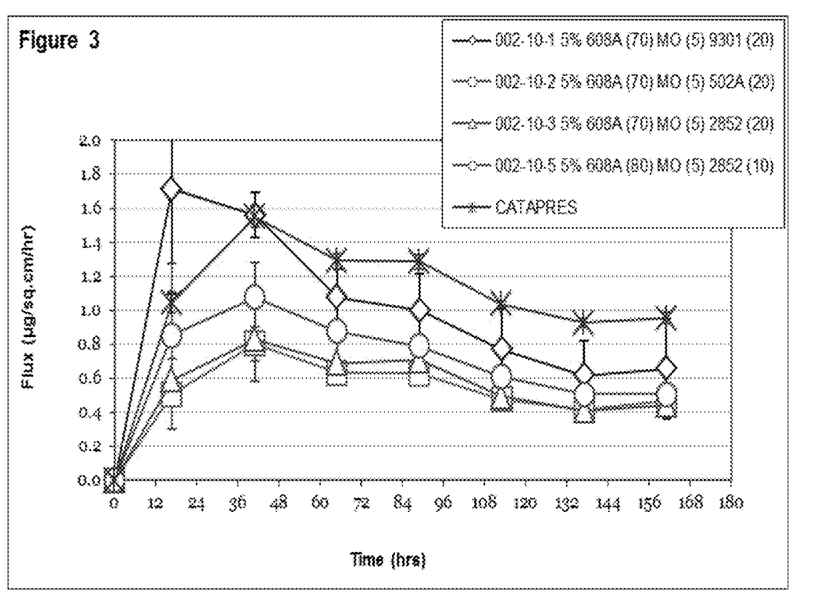
FIG. 3 is a release profile of Flux v. time of embodiments of the present invention.
Figure 4:
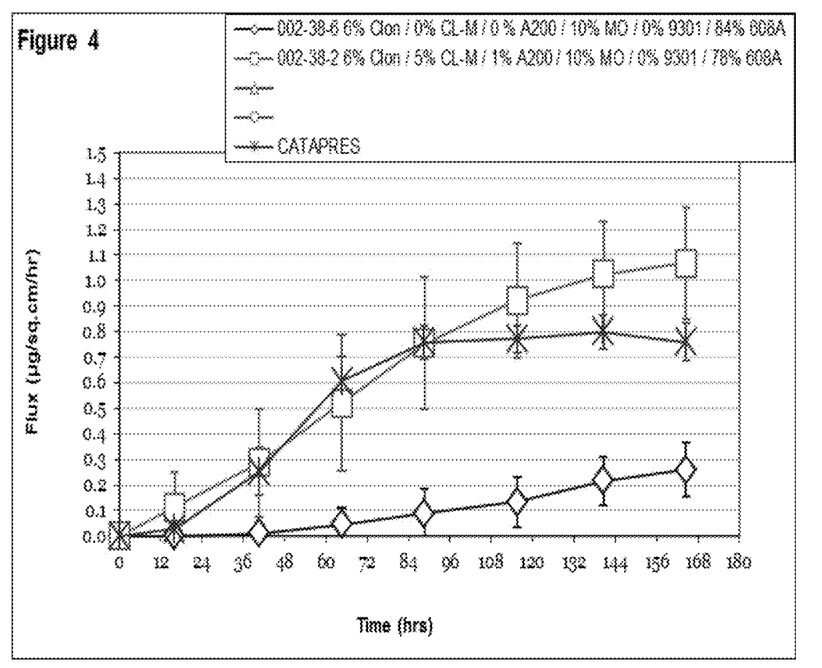
FIG. 4 is a release profile of Flux v. time of embodiments of the present invention.

In FIG. 3, all formulations exhibit a "dump and die" delivery profile as compared to the control and the 002-7-5 formulation containing insoluble PVP.

This is the first concept of insoluble PVP providing significant sustained delivery improvements over standard formulation techniques for dispersed API formulations.

Skin Permeation Study #0007:

Formulations consisted of the base formulations with insoluble PVP with various filling agents to increase the cohesion of the adhesive matrix. Primary determinant is the type and concentration of filler. As well, FIG. 1 confirms the flux from the previous study.

| Ingredients | 32-1 | 32-2 | 32-3 | 32-4 | 32-5 | 32-6 | 33-2 | 33-3 |
|---|---|---|---|---|---|---|---|---|
| Clonidine Base | 6% | 6% | 6% | 6% | 6% | 6% | 6% | 6% |
| PIB PSA 87-608A | 79% | 77% | 77% | 77% | 77% | 77% | 78% | 74% |
| Mineral Oil | 10% | 10% | 10% | 10% | 10% | 10% | 10% | 10% |
| Crospovidone | 5% | 5% | 5% | 5% | 5% | 5% | 5% | 5% |
| KAOLIN | | 2% | | | | | | |
| TITANIUM DIOXIDE | | | 2% | | | | | |
| AEROSIL® 200 | | | | | 2% | | 1% | 5% |
| AEROSIL® 300 | | | | | | 2% | | |
| AEROSIL® R972 | | | | | | 2% | | |

Results are shown in the figures. Formulations 002-32 and 002-33 were the first formulations made with the BASF Kollidon® CL-M material.

Figure 21:
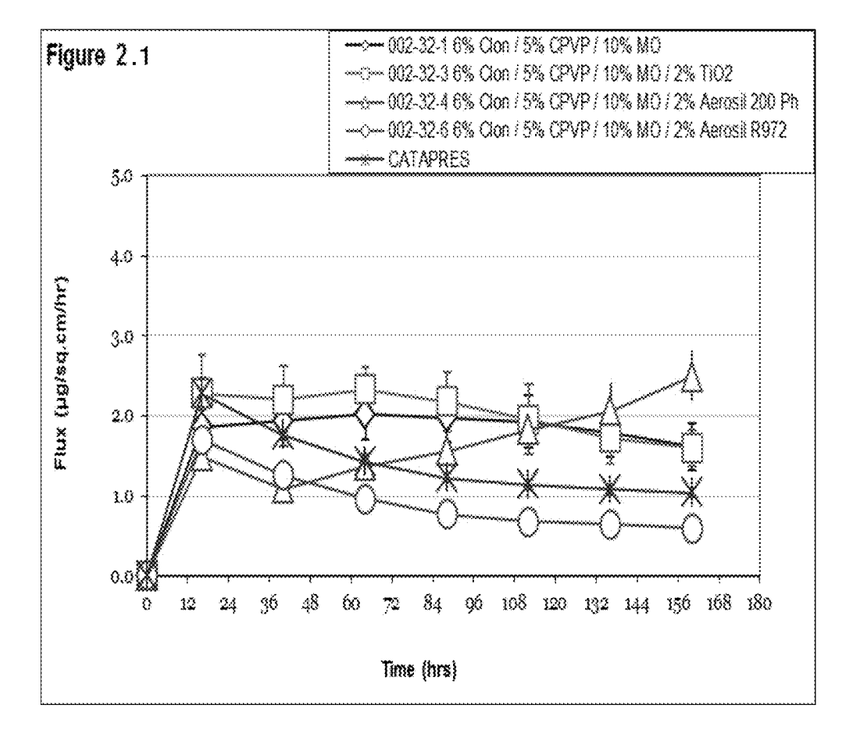

FIG. 2.1 exhibits the addition of various fillers to increase cohesive forces within the formulations. As can be seen TiO2, does not affect flux compared to the control formula. The R972 SiO2 significantly reduces the flux over 7 days. Interestingly, at the 2% level the Aerosil® pharma 200 SiO2 actually reduces the dump/onset, but significantly increases the sustained delivery through 7 days.

Figure 31:
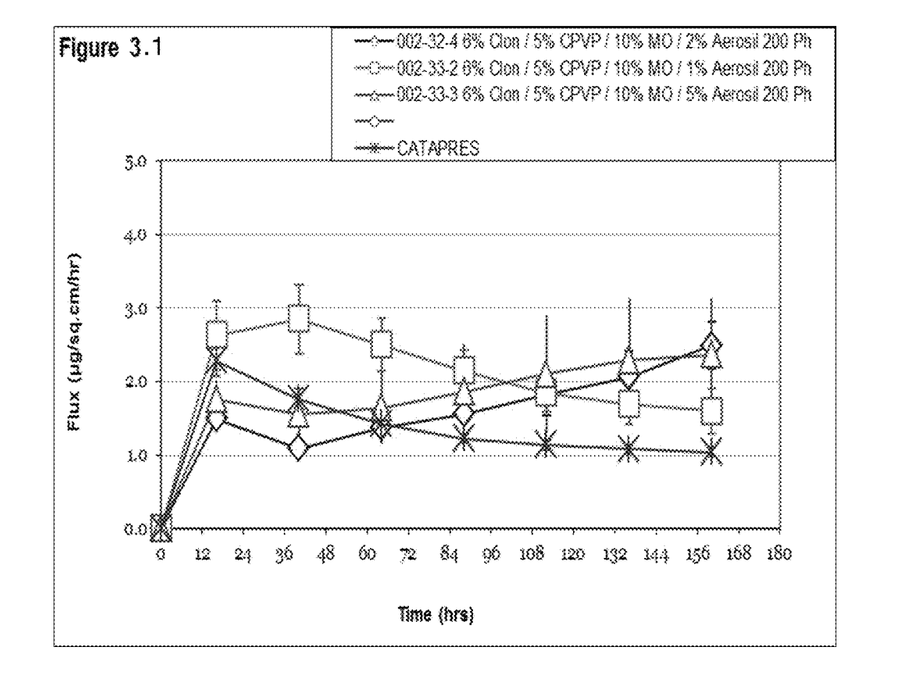
Figure 41:
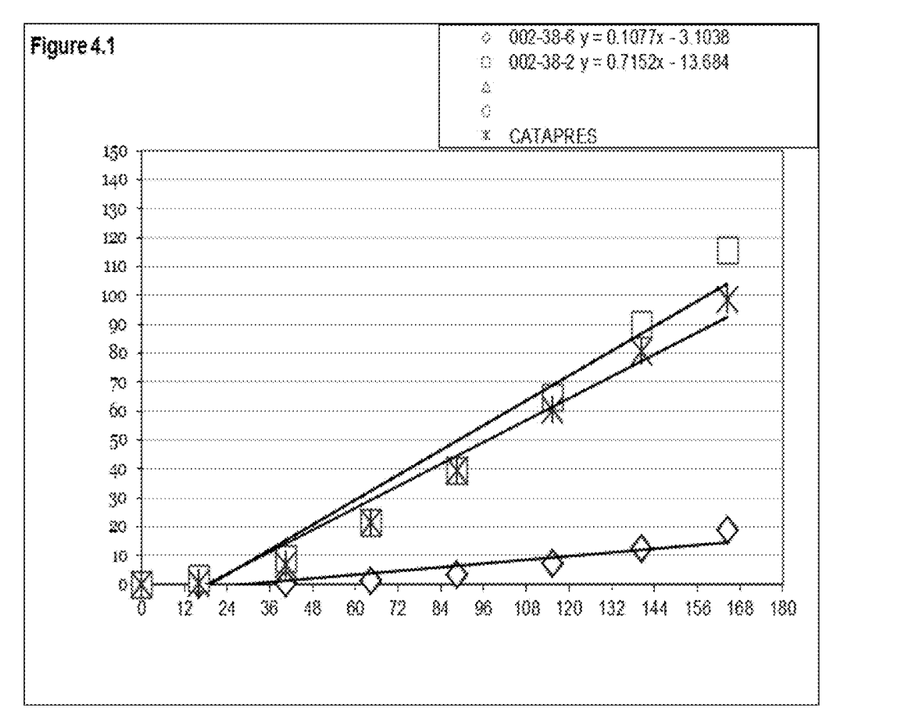

FIG. 3.1 exhibits the addition of levels of the Aerosil® 200 Pharma as a filler. It can be observed at greater than 2% levels the flux is impeded. At 1% level, the formulation seems to be equivalent to the control, with the benefit of having a potentially smaller patch size.

Preferred Formulation Ranges:
Clonidine Base—5% to 10%
Crospovidone—1% to 15%
silicon dioxide—0.5% to 5%
Mineral Oil—1% to 20%
PIB formulated adhesive—40% to 95%

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A transdermal formulation comprising:
   an active pharmaceutical ingredient, wherein said active pharmaceutical ingredient is clonidine;
   a polyisobutylene pressure sensitive adhesive, wherein said polyisobutylene pressure sensitive adhesive is present in an amount ranging from about 50-99.6% w/w;
   a binder, wherein said binder is cross-linked polyvinylpyrrolidone;
   a filler, wherein said filler comprises silicon dioxide, wherein the silicon dioxide is present in an amount ranging from about 2-5% w/w, further wherein the ratio of the silicon dioxide to cross-linked polyvinylpyrrolidone ranges from about 1:1 to about 1:5; and
   mineral oil;
   wherein said formulation is a component of a transdermal delivery system that delivers said active pharmaceutical ingredient for up to seven days, wherein delivery of the active pharmaceutical ingredient increases over the seven days.

2. The formulation of claim 1 wherein said active pharmaceutical ingredient is delivered at therapeutic levels for up to 7 days.

3. The formulation of claim 1 wherein said active pharmaceutical agent is present in an amount ranging from about 0.1-15% w/w.

4. The formulation of claim 1 wherein said binder is present in an amount ranging from about 0.1-15% w/w.

5. The formulation of claim 1 wherein said mineral oil is present in an amount ranging from 1-20% w/w.

6. The formulation of claim 1 wherein said formulation exhibits an increasing flux between 36 hours and 156 hours.

7. A method of providing transdermal delivery of an active pharmaceutical ingredient to a patient for up to seven days, the method comprising:
   providing a transdermal delivery patch including the transdermal formulation of claim 1, wherein the transdermal delivery patch includes a backing layer, a single adhesive layer comprising the transdermal formulation of claim 1, and a release liner;
   affixing said patch to the patient; and
   transdermally delivering the active pharmaceutical ingredient to the patient.

* * * * *